United States Patent [19]

Skrabanja et al.

[11] Patent Number: 5,656,597
[45] Date of Patent: Aug. 12, 1997

[54] LYOSPHERES COMPRISING GONADOTROPIN

[75] Inventors: Arnold Titus Philip Skrabanja, Nijmegen; Herman Vromans, Oss, both of Netherlands

[73] Assignee: Akzo Nobel N.V., Arnhem, Netherlands

[21] Appl. No.: 454,333

[22] PCT Filed: Apr. 25, 1994

[86] PCT No.: PCT/EP94/01303

§ 371 Date: Jun. 5, 1995

§ 102(e) Date: Jun. 5, 1995

[87] PCT Pub. No.: WO94/25005

PCT Pub. Date: Nov. 10, 1994

[30] Foreign Application Priority Data

Apr. 28, 1993 [EP] European Pat. Off. ............ 93201215

[51] Int. Cl.⁶ ........................... C07K 14/59; A61K 38/24
[52] U.S. Cl. ......................... 514/12; 514/21; 530/398
[58] Field of Search ................ 530/398; 514/12, 514/21

[56] References Cited

U.S. PATENT DOCUMENTS 3,932,943  1/1976  Briggs et al. ........................... 34/5

FOREIGN PATENT DOCUMENTS 0 081913  6/1983  European Pat. Off. .
0 448146  9/1991  European Pat. Off. .
2 160528  12/1985  United Kingdom .
WOA9013285  11/1990  WIPO .

Primary Examiner—Howard E. Schain
Attorney, Agent, or Firm—Gregory R. Muir; William M. Blackstone

[57] ABSTRACT

The invention relates to lyospheres comprising gonadotropin, the preparation thereof, as well as pharmaceutical preparations containing the same.

10 Claims, No Drawings

LYOSPHERES COMPRISING GONADOTROPIN

The invention relates to lyospheres comprising gonadotropin, the preparation thereof, as well as pharmaceutical preparations comprising the same.

Lyospheres are freeze-dried droplets. Spherical freeze-dried particles are known from Price et al. (U.S. Pat No. 3,655,838). These spherical beads, contain material for immunological reactions. Lyospheres comprising biological active materials are known, for instance from U.S. Pat. No. 3,932,943, and also from many other patents. Known advantages of lyospheres are the uniformity of the particles, the easy to handle products, the faster freeze-dry process, less degradation during the freeze-dry process, and the improved dissolution properties.

Surprisingly, it has now been found that lyospheres comprising gonadotropin have an improved shelf-life in comparison to conventionally freeze-dried gonadotropins. Moreover, as additional advantages it has been found that the recovery of the gonadotropin after freeze-drying of the lyospheres is better than the recovery after conventional freeze-drying, and that the analysis properties are improved.

The invention therefore, relates to a lyosphere which comprise a gonadotropin. Preferably said gonadotropin is HCG (human chorionic gonadotropin), FSH (follicle stimulating hormone), or LH (luteinizing hormone), or a combination thereof. Said gonadotropins may obtained by isolation from natural sources or by recombinant techniques. With most preference, said gonadotropin is rec-FSH.

The lyospheres may also comprise pharmaceutically acceptable auxiliaries, such as fillers, stabilizers, and surfactants. Usual auxiliaries are for example sucrose, mannose, trehalose, dextran, Tween, polyvinyl pyrrolidone, sodium citrate and the like.

The lyospheres can be prepared by freeze-drying droplets of an aqueous gonadotropin solution, which optionally also comprises the auxiliaries. To obtain droplets of the required size, the solution can be sprayed into a cold bath (for example as disclosed in DT 2,140,747, EP 81913, or U.S. Pat. No. 3,928,566), into liquid nitrogen (for example as disclosed in J5 9169,504), or onto a refrigerated drum (for example as disclosed in U.S. Pat. No. 3,892,876) or a refrigerated plate (for example as disclosed in U.S. Pat. No. 4,501,719). Various other methods are well-known in the art.

The lyospheres of the invention can be processed into a pharmaceutical preparation. The term pharmaceutical preparation means a vial or syringe, or any other means in which the lyospheres can be introduced, and as such can be used by physicians. When the lyosphere comprises FSH or rec-FSH as the gonadotropin, pharmaceutical preparations comprise 75, 100, 150, 300, and preferably 50 IU of the FSH. Preferably each lyosphere comprises a fixed amount of gonadotropin, for instance 50 IU. Determination of the amount of IU's present in the pharmaceutical preparation can then simply achieved by counting the number of lyospheres. When the lyosphere contains hCG or rec-CG as the gonadotropin, pharmaceutical preparations comprise preferably 1, 2.5, 5, 10, or 5000 IU of the gonadotropin.

The lyospsheres of the invention may be used for medical applications where gonadotropins are required. The lyospheres containing FSH or rec-FSH are particularly useful for application in IVF (in vitro fertilisation). The invention is further illustrated by the following examples.

EXAMPLE 1

Lyospheres were prepared as follows. The ingredients (gonadotropin and the expedients sucrose or trehalose, polysorbate 20, and possibly sodium citrate) were dissolved in water and diluted to the desired final concentration. The pH was adjusted to 7 using hydrochloric acid and/or sodium hydroxide. After filtration through a disposable 0.2 µm Durapore membrane filter, 100 µl droplets were formed and frozen, for instance in liquid nitrogen. The frozen droplets were collected and freeze-dried at −50° C. in a manner known per se. The freeze-dried droplets (lyospheres) were transferred into an ampoule or vial.

EXAMPLE 2

The recovery of freeze-drying of lyospheres and conventional freeze-drying was compared by EIA (enzyme immuno assay) using aqueous formulations containing 10 U of rec-HCG.
Result:

| formulation | content of HCG in U after freeze-drying | |
|---|---|---|
| | lyospheres | conventional |
| A | 10 | 7.4 |
| B | 9.9 | 7.2 |

Formulations per ml:
A: 50 mg of sucrose, 0.04 mg of Tween 20, 0.92 mg of sodium citrate, 10 U of rec HCG.
B: 50 mg of sucrose, 0.20 mg of Tween 20, 0.92 mg of sodium citrate, 10 U of rec HCG.

EXAMPLE 3

A 500 µl solution containing 75 IU of rec-FSH, 25 mg of sucrose, 7.35 mg of sodium citrate and 0.1 mg of polysorbate 20 was conventionally freeze-dried and compared with a 100 µl solution containing 75 IU of rec-FSH, 25 mg of sucrose, 7.35 mg of sodium citrate and 0.02 mg of polysorbate 20 which was freeze-dried as a lyosphere. Both freeze-dried products were stored for 6 months at 4°, 25°, 30°, 40°, and 50° C., and for 12 months at 4°, 25° and 30° C. After 6 and 12 months the in vitro activity was determined according to the method of Mannaerts et al. in Roland et al. (ed.): Neuroendocrinology of reproduction, 1987, p.49–58, and expressed as percentage of the activity of the sample stored at 4° C.:

| | lyosphere | | conventional | |
|---|---|---|---|---|
| | activity in % | | | |
| temp in °C. | 6 | 12 | 6 | 12 months |
| 4 | 100 | 100 | 100 | 100 |
| 25 | — | 96 | 102 | 73 |
| 30 | 118 | 85 | 97 | 77 |
| 40 | 118 | — | 76 | — |
| 50 | 100 | — | 50 | — |

EXAMPLE 4

A 500 µl solution containing 5 IU of rec-HCG, 25 mg of sucrose, 0.46 mg of sodium citrate and 0.1 mg of polysorbate 20 was conventionally freeze-dried and compared with a 100 µl solution containing 5 IU of HCG, 25 mg of sucrose, 0.46 mg of sodium citrate and 0.02 mg of polysorbate 20 which was freeze-dried as a lyosphere. Both freeze-dried products were stored for 2 months at −18° and 50° C. After 2 months the activity was determined by EIA and expressed as percentage of the activity of the sample stored at −18° C.:

| temp in °C. | activity in % | |
| --- | --- | --- |
| | lyosphere | conventional |
| −18 | 100 | 100 |
| 50 | 84 | 59 |

EXAMPLE 5

A 500 μl solution containing 5 IU of urinary HCG, 25 mg of sucrose, 0.46 mg of sodium citrate and 0.1 mg of polysorbate 20 was conventionally freeze-dried and compared with a 100 μl solution containing 5 IU of urinary HCG, 25 mg of sucrose, 0.46 mg of sodium citrate and 0.02 mg of polysorbate 20 which was freeze-dried as a lyosphere. Both freeze-dried products were stored for 2 or 6 months at −18°, 8°, 30°, and 50° C. After 2 or 6 months the activity was determined by EIA and expressed as percentage of the activity of the sample stored at −18° C.:

| | activity in % | | |
| --- | --- | --- | --- |
| | lyosphere | | conventional |
| temp in °C. | month 2 | 6 | 2 |
| −18 | 100 | 100 | 100 |
| 8 | 100 | 100 | — |
| 30 | 100 | 93 | 82 |
| 50 | 82 | 78 | 25 |

We claim:

1. A lyosphere comprising a gonadotropin.
2. The lyosphere of claim 1, wherein the gonadotropin is selected from the group consisting of HCG, natural purified FSH, recombinant FSH, LH, and a combination of two or more thereof.
3. The lyosphere of claim 1, wherein the gonadotropin is mixed with pharmaceutically acceptable auxiliaries.
4. The lyosphere any one of claim 1 for use in IVF.
5. The lyosphere of claim 1, wherein the gonadotropin is freeze-dried as a droplet.
6. A pharmaceutical preparation comprising lyospheres according to claim 1 and a pharmaceutically acceptable additive.
7. The pharmaceutical preparation of claim 6, wherein the lyospheres comprise 50 IU of natural purified FSH or recombinant FSH.
8. The lyosphere of claim 3, wherein the gonadotropin and pharmaceutically acceptable auxiliaries are freeze-dried together as a droplet.
9. The lyosphere of claim 5, wherein the gonadotropin is selected from the group consisting of HCG, natural purified FSH, recombinant FSH, LH and a combination of two or more thereof.
10. The lyosphere of claim 8, wherein the gonadotropin is selected from the group consisting of HCG, natural purified FSH, recombinant FSH, LH and a combination of two or more thereof.

\* \* \* \* \*